(12) United States Patent
Beyens

(10) Patent No.: US 9,116,054 B2
(45) Date of Patent: Aug. 25, 2015

(54) DROP-IN PROBE

(75) Inventor: Dries Beyens, Kinrooi (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 52 days.

(21) Appl. No.: 13/375,829

(22) PCT Filed: Jun. 1, 2010

(86) PCT No.: PCT/EP2010/003310
§ 371 (c)(1),
(2), (4) Date: Dec. 2, 2011

(87) PCT Pub. No.: WO2010/139453
PCT Pub. Date: Dec. 9, 2010

(65) Prior Publication Data
US 2012/0082183 A1   Apr. 5, 2012

(30) Foreign Application Priority Data

Jun. 5, 2009 (DE) .......................... 10 2009 024 265
Dec. 18, 2009 (DE) .......................... 10 2009 059 780

(51) Int. Cl.
*G01K 1/12* (2006.01)
*G01K 7/00* (2006.01)
(Continued)

(52) U.S. Cl.
CPC .............. *G01K 13/125* (2013.01); *G01N 25/04* (2013.01); *C22B 9/006* (2013.01)

(58) Field of Classification Search
USPC .......................................... 374/179, E07.004
See application file for complete search history.

(56) References Cited

U.S. PATENT DOCUMENTS 3,463,005 A   8/1969 Hance
3,577,886 A   5/1971 Wiese
(Continued)

FOREIGN PATENT DOCUMENTS

CN   201041556 Y   3/2008
DE   3919362 C2   12/1990

OTHER PUBLICATIONS

Int'l Search Report and Written Opinion issued Oct. 29, 2010 in Int'l Application No. PCT/EP2010/003310.
(Continued)

*Primary Examiner* — Lisa Caputo
*Assistant Examiner* — Nasir U Ahmed
(74) *Attorney, Agent, or Firm* — Panitch Schwarze Belisario & Nadel LLP

(57) ABSTRACT

A drop-in probe is provided for determining phase changes of a sample removed from a molten steel by thermal analysis. The probe includes a measurement head that has an immersion end and in which is arranged a sample chamber having an inlet opening and a thermocouple projecting with its hot solder joint into the sample chamber and having a cable bushing for signal cables of the thermocouple. The cable bushing emerges from the measurement head out of a discharge opening on an end of the measurement head opposite the immersion end. A straight line between the immersion end and the discharge opening forms a longitudinal axis of the measurement head, and a theoretical plane through the hot solder joint and through a part of the inlet opening farthest away from the immersion end is formed perpendicular to the longitudinal axis. The probe is characterized by either a) the measurement head has a density of at least 7 $g/cm^3$ between the immersion end and the plane farthest away from the immersion end or b) the measurement head has a density of at least 7 $g/cm^3$ between the immersion end and an auxiliary plane formed at a distance of at least 10 mm and parallel to the plane farthest away from the immersion end.

22 Claims, 5 Drawing Sheets

(51) Int. Cl.
*G01K 13/12* (2006.01)
*G01N 25/04* (2006.01)
*C22B 9/00* (2006.01)

(56) References Cited

U.S. PATENT DOCUMENTS

| | | | |
|---|---|---|---|
| 3,766,772 | A | 10/1973 | Kern et al. |
| 4,842,418 | A | 6/1989 | Conti |
| 4,881,824 | A | 11/1989 | Falk et al. |
| 5,033,320 | A | 7/1991 | Baerts |
| 5,275,488 | A | 1/1994 | Stelts |
| 5,577,841 | A * | 11/1996 | Wall .............................. 374/140 |
| 5,584,278 | A * | 12/1996 | Satoh et al. .................... 123/516 |
| 5,584,578 | A * | 12/1996 | Clauss, Jr. ...................... 374/140 |
| 6,299,348 | B1 * | 10/2001 | Theuwis ........................ 374/140 |
| 6,767,130 | B2 * | 7/2004 | Popelar et al. ................. 374/139 |
| 7,449,141 | B2 * | 11/2008 | Gerits ............................. 266/99 |
| 7,832,294 | B2 * | 11/2010 | Neyens ........................ 73/866.5 |
| 7,998,399 | B2 * | 8/2011 | Dams et al. ..................... 266/99 |

OTHER PUBLICATIONS

English translation of an Office Action issued Aug. 29, 2013 in CN Application No. 201080024812.X.

* cited by examiner

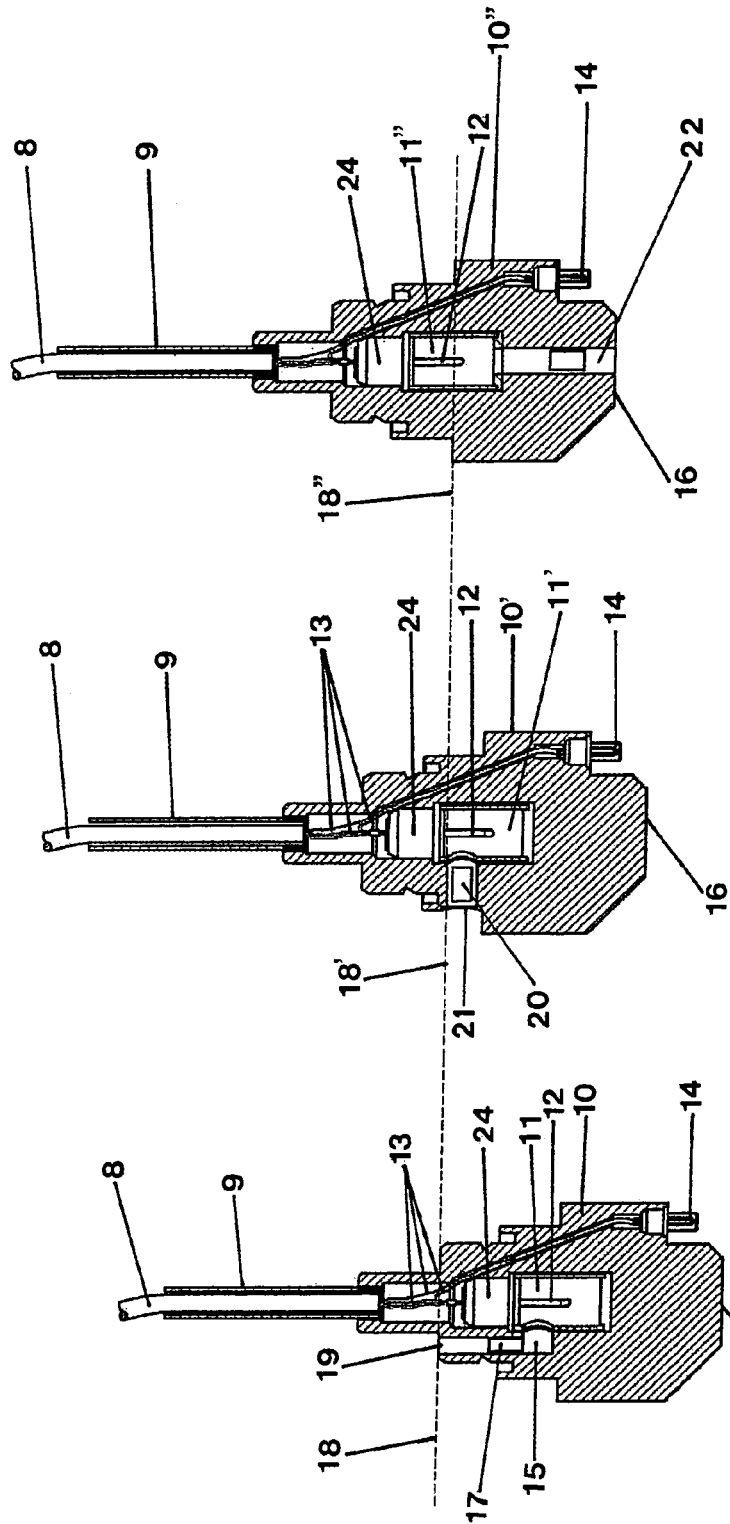

DROP-IN PROBE

CROSS-REFERENCE TO RELATED APPLICATION

This application is a Section 371 of International Application No. PCT/EP2010/003310, filed Jun. 1, 2010, which was published in the German language on Dec. 9, 2010, under International Publication No. WO 2010/139453 A1 and the disclosure of which is incorporated herein by reference.

BACKGROUND OF THE INVENTION

The invention relates to a drop-in probe for determining phase changes of a sample removed from a molten steel by thermal analysis, with a measurement head having an immersion end, in which is arranged a sample chamber having an inlet opening and a thermocouple projecting into the sample chamber with its hot solder joint and that has a cable bushing for signal cables of the thermocouple, wherein, on one end of the measurement head opposite the immersion end, the cable bushing emerges from this measurement head out of an outlet opening, and wherein a straight line between the immersion end and the outlet opening forms a longitudinal axis of the measurement head.

Such probes are known, for example, from U.S. Pat. No. 3,463,005. Here, a probe is described that is dropped into a molten metal from a great height on a signal cable. For stabilization, the measurement head has a paperboard tube on its end facing away from the immersion end, with the signal cable being guided through this tube. A thermocouple is arranged on the immersion end of the probe. An additional thermocouple is arranged on the side in a chamber formed of refractory material and is used for determining the liquidus curve. An additional drop-in probe is known from U.S. Pat. No. 4,881,824. It has, on its front end, a thermocouple as well as, on the side, a sample holding chamber. A similar drop-in probe is described in U.S. Pat. No. 5,275,488. For this probe, a thermocouple projecting from the measurement head is arranged on its immersion end. It is protected by metal braces that form a kind of cage on the immersion end of the probe.

Immersion probes that are immersed in the melt by means of a carrier tube that can be placed on a so-called lance are known, for example, from U.S. Pat. No. 4,842,418 or U.S. Pat. No. 5,577,841. The devices described there each have a sample chamber on their front end. Another immersion probe is described in German Patent DE 39 19 362 C2. Here, a sample chamber for measuring the liquidus temperature is arranged in a carrier tube. A sensor for determining the carbon content of molten metal in converter furnaces is known from Chinese published patent application CN 201041556 Y.

BRIEF SUMMARY OF THE INVENTION

The object of the invention is to provide an improved drop-in probe, in order to allow more precise measurements, in particular, in a converter.

The object is achieved by a drop-in probe of the type described at the outset, wherein the measurement head between its immersion end and a plane vertically cutting the line between the immersion end and the outlet opening has a density of at least 7 g/cm$^3$, wherein the inlet opening opens between this plane and the immersion end or at the immersion end, and wherein the total density of the measurement head equals less than 7 g/cm$^3$. Advantageously, a theoretical plane through the hot solder joint and through a part of the inlet opening arranged farthest away from the immersion end is formed vertical to the longitudinal axis, and wherein either a) the measurement head between the immersion end and the plane farthest away from the immersion end has a density of at least 7 g/cm$^3$ or b) the measurement head between the immersion end and an auxiliary plane that is formed parallel to and at a distance of at least 10 mm from the plane farthest away from the immersion end has a density of at least 7 g/cm$^3$, whereby the probe can penetrate the slag lying on the molten metal in a vertical position and can be immersed vertically into the molten metal. The auxiliary plane is preferably arranged between the plane farthest away from the immersion end and the immersion end.

With the immersion probe according to embodiments of the invention, it is possible to analyze the carbon content of the molten metal in a converter (BOF boiler) by measuring the liquidus temperature. This can be realized in the converter during the blowing process. Simultaneously, the temperature of the molten steel can be measured. Through the ability to perform the measurements during the blowing process, the entire process can be optimized, so that it is prevented that too much gas is blown into the melt. The probe penetrates nearly vertically into the molten metal. The measurement head can be made from several steel bodies arranged one behind the other in the immersion direction.

The measurement head is a body that is formed essentially from metal, preferably steel, and that extends between the immersion end and the cable outlet. In addition to its metal body, the measurement head comprises the volume and material of the thermocouple, the sample chamber, and the inlet opening. The latter is constructed as a tube. The form of the metal body is defined by its silhouette, wherein the inlet opening of the sample chamber and the outlet opening of the signal cable are considered to be closed.

It is advantageous that the inlet opening have a diameter that equals at least one third of the diameter of the sample chamber and is at most as large as the diameter of the sample chamber.

The distance of the auxiliary plane from the plane farthest away from the immersion end preferably equals at least 20 mm, in particular at least 30 mm. The auxiliary plane lies advantageously between the immersion end and the plane farthest away from the immersion end. Therefore, the center of gravity of the immersion probe lies relatively far forward on the immersion end of the measurement head.

The thermocouple extends preferably somewhat parallel to the longitudinal axis with its hot solder joint in the direction of the immersion end. It is further preferred that the thermocouple be held with a gas-permeable material in the sample chamber. The cable bushing and the outlet opening via the gas-permeable material are also preferably connected in a gas-permeable way to the sample chamber, so that gases can be discharged nearly unimpaired from the sample chamber, in particular it is also advantageous that a tube, advantageously a metal tube, advantageously running coaxial to the straight line, be arranged at the outlet opening, wherein the signal cables are guided through this tube. It is used for the additional stabilization of the measurement probe while it is being dropped in and for the temporary protection of the signal cables before the early destruction in the molten metal.

It is further preferred that the inlet opening have, on its outer side, a protective cap formed from metal or a combination of metal with cardboard or with paper. In this way, the early penetration of material into the sample chamber is prevented before the inlet opening arrives beneath the bath level of the molten metal. The protective cap is advantageously formed from steel; it preferably has a thickness of at most 0.5 mm; likewise the protective cap can be formed from a combination made of zinc with cardboard or with paper or of steel with a coating made of zinc. The inlet opening is advantageously formed from quartz glass. In the inlet opening, a deoxidizing agent can be arranged. Here, for example, aluminum is to be named as a suitable material.

Another preferred construction of the drop-in probe according to an embodiment of the invention distinguishes itself in that the measurement body is formed essentially from metal, preferably steel. Alternatively, the measurement body could also be formed from a cast part. Here, cast iron or gray cast iron is especially suitable. The additional elements, such as thermocouples, sample chambers, etc., can then be integrated into measurement heads constructed in this way. The stated materials allow long-term structural stability of the measurement head, even in molten steel, so that the molten steel flowing into the sample chamber can solidify and a reliable and reproducible measurement can be produced. Advantageously, the sample body has a volume of at least 450 $cm^3$. In connection with the total density of the measurement head constructed according to embodiments of the invention, it is thus ensured that the measurement head can operate in the liquid molten steel for a sufficient length of time in a functionally reliable way.

When the measurement head is immersed into the molten steel, some flows through an inlet opening into the sample chamber of the measurement head. The dimensions of the sample chamber must be selected so that rapid cooling of the molten metal can be ensured. Because the connection cables between the measurement head and the evaluation electronics are melted through after an average time period of 8-10 seconds, a reproducible solidification of the liquid metal in the sample chamber must take place in this time span, in order to perform the necessary measurements. Sample chambers having a volume between 7 and 50 $cm^3$ have proven especially advantageous. In order to ensure a uniform flow of the liquid molten steel into the sample chamber, it is advantageous if the latter has a gas discharge opening. The air forced from the molten steel can leave the sample chamber through any gas discharge opening and thus make room for the pressing-in molten steel. Advantageously, any gas discharge opening is located on an upper side of the measurement head according to the invention. In a particularly advantageous construction, the gas discharge opening is formed by a gap, which is arranged between the signal cable and a metal tube. The latter metal tube here protects the signal cable from premature damage by the slag and/or the molten steel.

One advantageous embodiment of the invention distinguishes itself in that the total density of the measurement head equals less than 7 $g/cm^3$. Here, only the volume and the weight of the measurement head are taken into account.

Another advantageous embodiment of the invention distinguishes itself in that the total density of the part of the drop-in probe immersed in the molten steel and the slag has a total density of less than 7 $g/cm^3$. For this variant embodiment the measurement head also comprises a metal tube at least partially surrounding the signal cable and parts of the signal cable, in so far as these parts are also immersed in the molten steel and the slag. In one advantageous variant of this embodiment of the invention, the total density of the measurement head and 50 cm of a signal cable having an average cable density of 1.6 $g/cm^3$ amounts to less than 7 $g/cm^3$. Thus, the total density in this embodiment relates to not only the measurement head of the drop-in probe, but also a defined length of the signal cable. The length—0.5 m—of the signal cable is given from the preferred measurement position of the measurement head, approximately 20 cm beneath the surface of the molten metal. For the positioning of the measurement head, the buoyant force of the cable within the slag on the molten steel must also be taken into account. Its thickness equals, in general, approximately 30 cm. Therefore, it is required according to the invention that, for the calculation of the total density of less than 7 $g/cm^3$, those parts of the drop-in probe that are immersed in the molten steel and/or the slag are also taken into account. In this embodiment variant the measurement head also comprises a metal tube at least partially surrounding the signal cable. The cable outlet is the location where the signal cable leaves this metal tube.

The drop-in probe can have an additional temperature sensor, with which the bath temperature can be determined independently. The additional temperature sensor can be arranged, among other places, on the end of the measurement head opposite the immersion end.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 2 is side elevation sectional view through the measurement head of a drop-in probe according to an embodiment of the invention;

FIG. 3 is a view similar to FIG. 2 of an additional embodiment of a drop-in probe according to the invention;

FIG. 4 is a view similar to FIG. 2 of an additional drop-in probe according to the invention with front inlet;

DETAILED DESCRIPTION OF THE INVENTION

Figure 1:
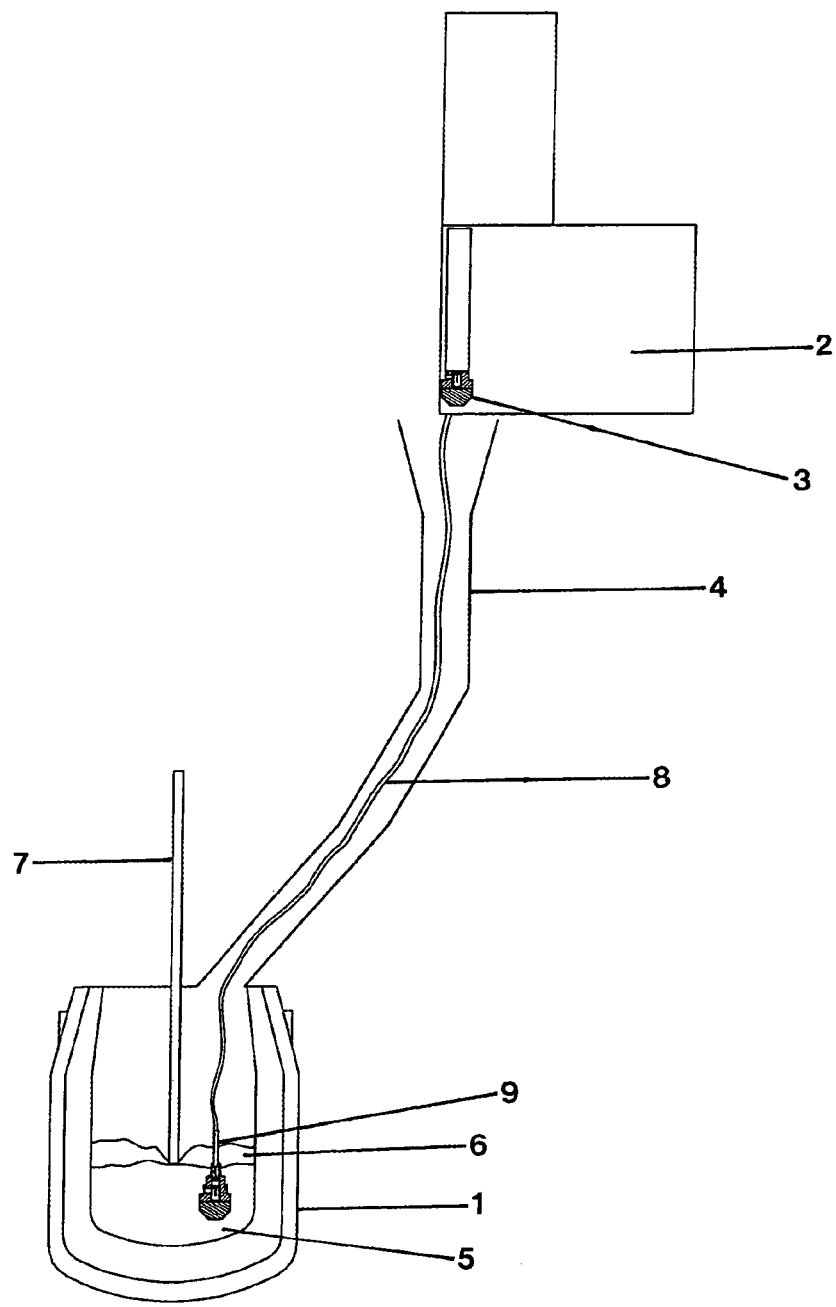
FIG. 1 is a schematic elevation view showing the relationship of the drop-in of a drop-in probe in a converter.

In the overview shown in FIG. 1, a drop device 2 is arranged a few meters above a converter 1; the drop device 2 is used as storage for the drop-in probes 3. The drop-in probes 3 are automatically released from the storage; they fall through a guide 4 into the converter 1 and into the molten steel 5 located in this converter after they have penetrated the slag layer 6 lying above the molten steel. In FIG. 1 a blowing lance 7 is shown with which oxygen is blown into the molten steel. The drop-in probe 3 is connected to a signal cable 8 by which measurement signals can be led to a computer. The signal cable 8 is guided through a metal tube 9. The metal tube 9 protects the signal cable 8 from early damage due to the slag 6 or molten steel 5.

FIG. 2 shows a drop-in sensor with measurement head 10 made of steel. The measurement head 10 has a sample chamber 11 with a thermocouple 12. Above the sample chamber 11, the thermocouple lines 13 connected to the signal cable 8 are shown. Beyond the thermocouple lines 13 there is also an additional thermocouple 14 arranged on the outside of the measurement head 10 connected to the signal cable 8. The inlet opening 15 into the sample chamber 11 ends at the side facing the immersion end 16 of the measurement head 10, so that the insertion into the sample chamber 11 takes place from above after immersion of the measurement head 10 into the molten steel 5. A thin aluminum plate is arranged in the inlet opening 15 as a deoxidizing agent 17. Between the immersion end 16 and the plane 18 arranged on the upper end of the inlet opening 15, the density of the measurement head 10 equals 7.0 g/cm$^3$. The inlet opening 15 is formed essentially from a bent quartz-glass tube. The outer opening 19 of the inlet opening 15, through which the plane 18 runs, is formed with a protective cap that is not shown in the drawing, and that is formed from an approximately 0.2 to 0.4 mm thick steel plate that has a thin paperboard layer on its outer side.

In FIG. 3 a similar drop-in probe is shown. In contrast to the drop-in probe shown in FIG. 2, for the measurement head 10' shown in FIG. 3, the inlet 20 into the sample chamber 11' is arranged on the side. The outer opening of the inlet opening 20 is closed with a protective cap 21 made of a 0.4 mm thick steel cap coated with paperboard. The plane 18' runs through the top edge of the inlet opening 20. In FIGS. 2 and 3 the theoretical plane 18; 18' running through the top part of the respective inlet opening 15; 20 is farther away from the immersion end 16 than a theoretical plane, which is not shown in the drawing and which runs through the hot solder joint of the corresponding probe.

In the embodiment of a drop-in probe according to the invention shown in FIG. 4, compared with the FIGS. 2 and 3, the measurement head 10" is provided with an inlet opening 22, which opens starting from the sample chamber 11" in the immersion end 16 of the measurement head 10". Here, the theoretical plane 18" running through the hot joint of the thermocouple 12 is relevant for determining the density distribution. The density between the theoretical plane 18" and the immersion end 16 of the drop-in probe shown in FIG. 4 equals approximately 7.0 g/cm$^3$. In the embodiment shown in FIG. 3, the density between the theoretical plane 18' and the immersion end 16 equals approximately 7.1 g/cm$^3$.

Figure 5:
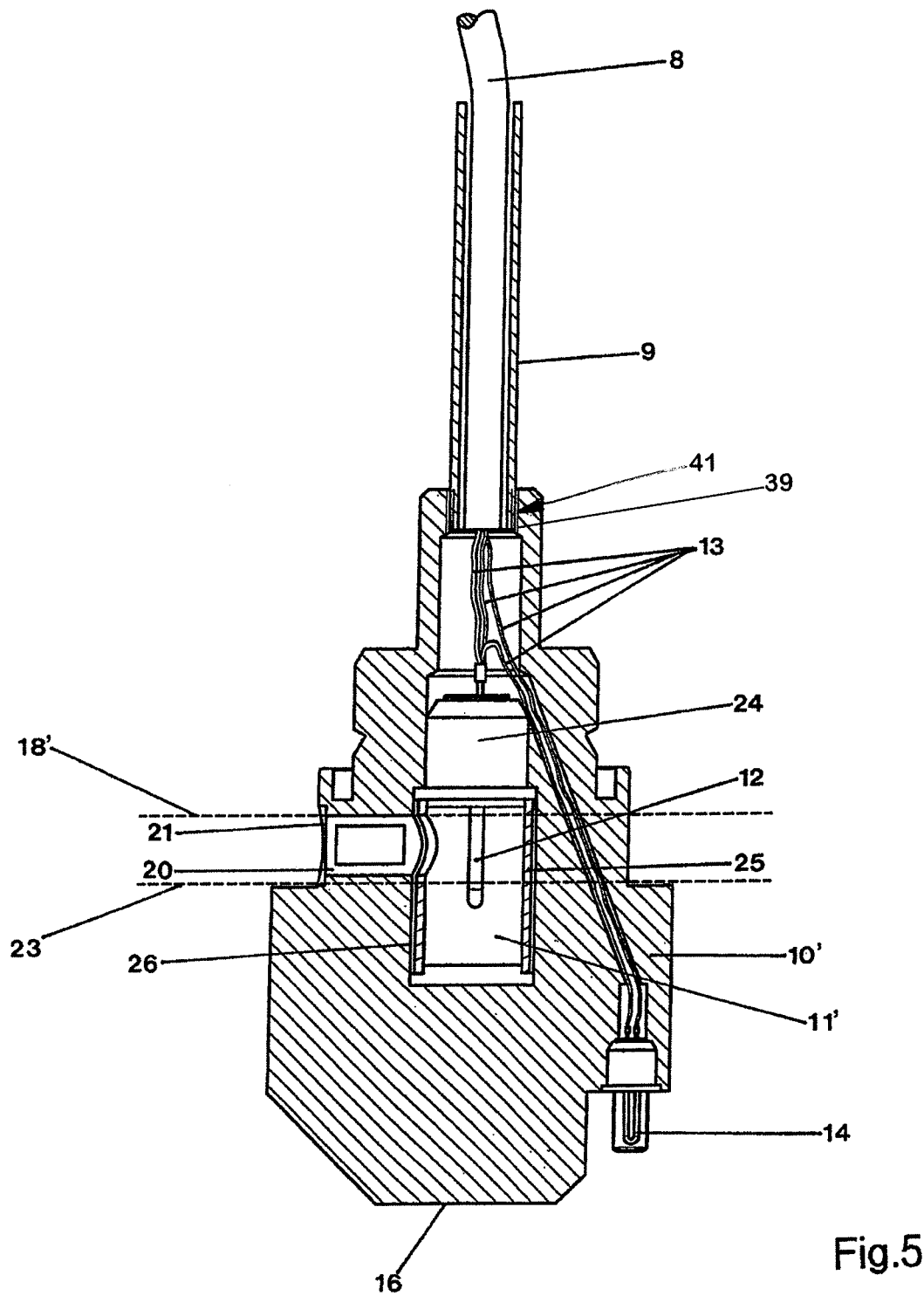
FIG. 5 is a view similar to FIG. 2 of a drop-in probe according to an embodiment of the invention with auxiliary plane.

The embodiment shown in FIG. 5, which in principle is similar to the embodiment shown in FIG. 3, was constructed so that the density between an auxiliary plane 23 and the immersion end 16 of the measurement head 10' equals approximately 7.4 g/cm$^3$, wherein the material of the measurement head 10' is formed essentially of steel. The auxiliary plane 23 is arranged approximately 15 mm below the theoretical plane 18' (in the direction of the immersion end 16).

The total density of the measurement head equals somewhat less than 6 g/cm$^3$. The measurement head is approximately 10 cm long, similarly with a greatest diameter of approximately 10 cm. The metal tube 9 is approximately 45 cm long. The signal cable length equals, in general, depending on the conditions of use, either 15 m or 26 m or even 35 m.

A refractory material 24 in which the thermocouple 12 is fixed is arranged above, that is, at a distance from the immersion end 16, onto the sample chamber 11; 11'; 11"; 11'''.

Figure 6:
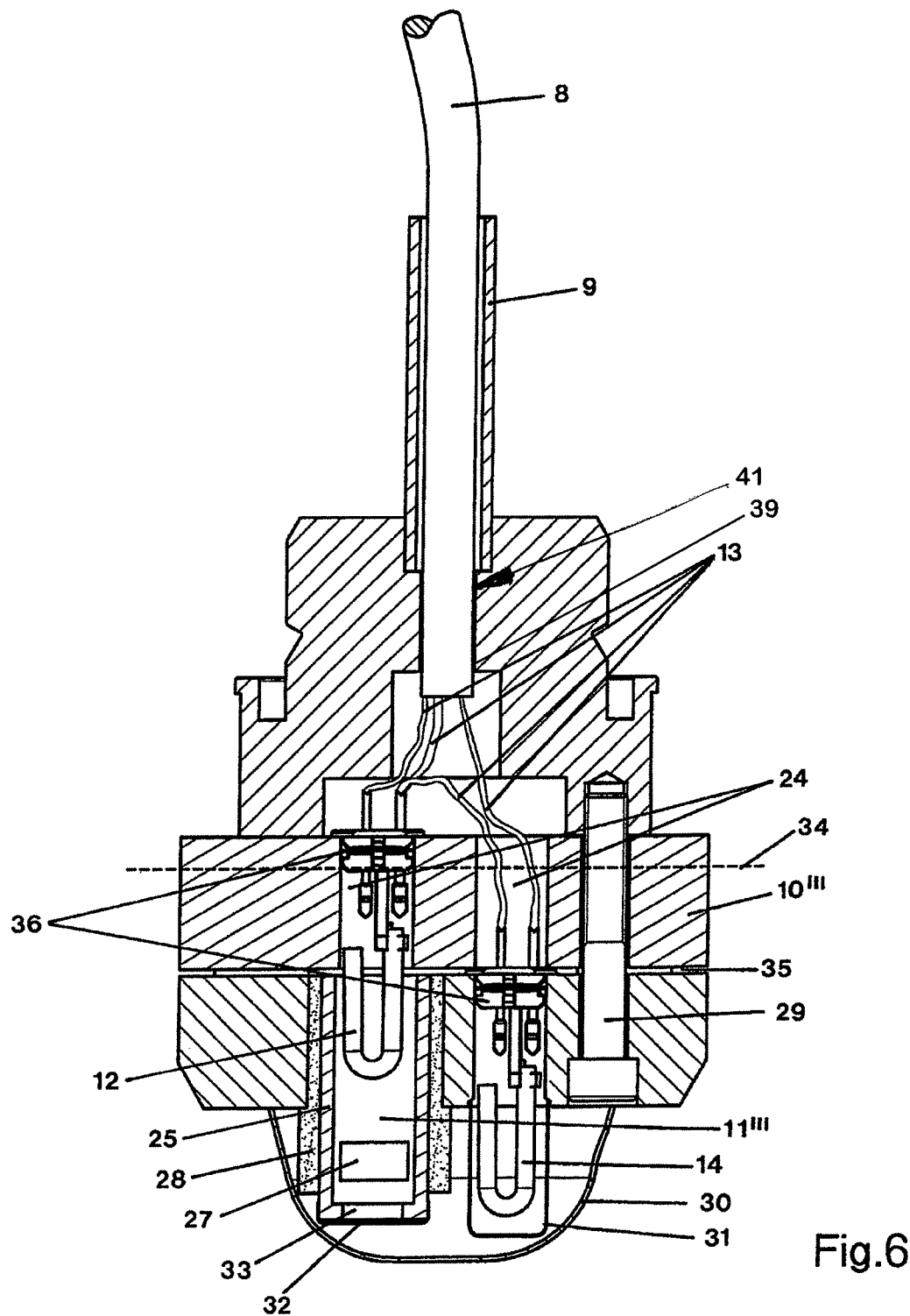
FIG. 6 is an elevation sectional section view of an additional drop-in probe according to an embodiment of the invention with front inlet.

In general, a protective cap 30, shown only in FIG. 6, can be arranged on the outside on the measurement head 10; 10'; 10"; 10'''. This is not to be taken into consideration in the determination of the density.

The refractory material 24 (for example, foundry sand or cement) is permeable to gas, but impermeable to the molten metal, so that gases can penetrate from the sample chamber through the refractory material 24. They are then discharged outward through the metal tube 9. A discharge opening 39 is formed on an end of the measurement head 10; 10'; 10"; 10''' opposite the immersion end 16 and a cable bushing 41 emerges from the measurement head out of the discharge opening 39. The sample chamber 11; 11'; 11"; 11''' is bounded at the sides, as can be seen in FIGS. 5, 6, by an insulating material 25. Between the insulating material 25 and the steel of the measurement head 10; 10'; 10"; 10''', a gap 26 of approximately 1 mm width is formed. The protective cap 21 can also be formed from thinner (approximately 0.2 mm thick) steel and can have, on the outer side, a layer made of cardboard, paper, or zinc.

The drop-in probe shown in FIG. 6 is essentially similar to the already described probes. The sample chamber 11''' is arranged on the immersion end of the measurement head 10'''. The inlet opening 33 has a diameter that equals approximately two thirds of the diameter of the sample chamber 11'''. It is closed with a metal cap 32 and fixed in the measurement head 10''' by foundry sand 28, wherein the foundry sand surrounds the sample chamber 11''' across the greatest part of its length also outside of the metal body. In the sample chamber 11''', a deoxidizing aluminum piece 27 is arranged. Next to the sample chamber 11''' there is a second thermocouple 14 that is covered with a metal cap 31. Both thermocouples 12; 14 are connected on their back end to a connector 36 by which the connection to the thermocouple lines 13 is realized. Between two parts of the metal body of the measurement head 10''' there are ventilation openings 35 for the sample chamber 11'''. The ventilation openings ensure a bubble-free sample. They can be constructed as individual boreholes or also as a peripheral gap between two separate parts of the metal body. In this case, the two parts are held together, for example, by screws 29. The front part of the measurement head 10''' is very heavy. Between its immersion end and the plane 34, it has a density of 7 g/cm$^3$ for a total density of the measurement head 10''' of 6.7 g/cm$^3$.

Figure 7:
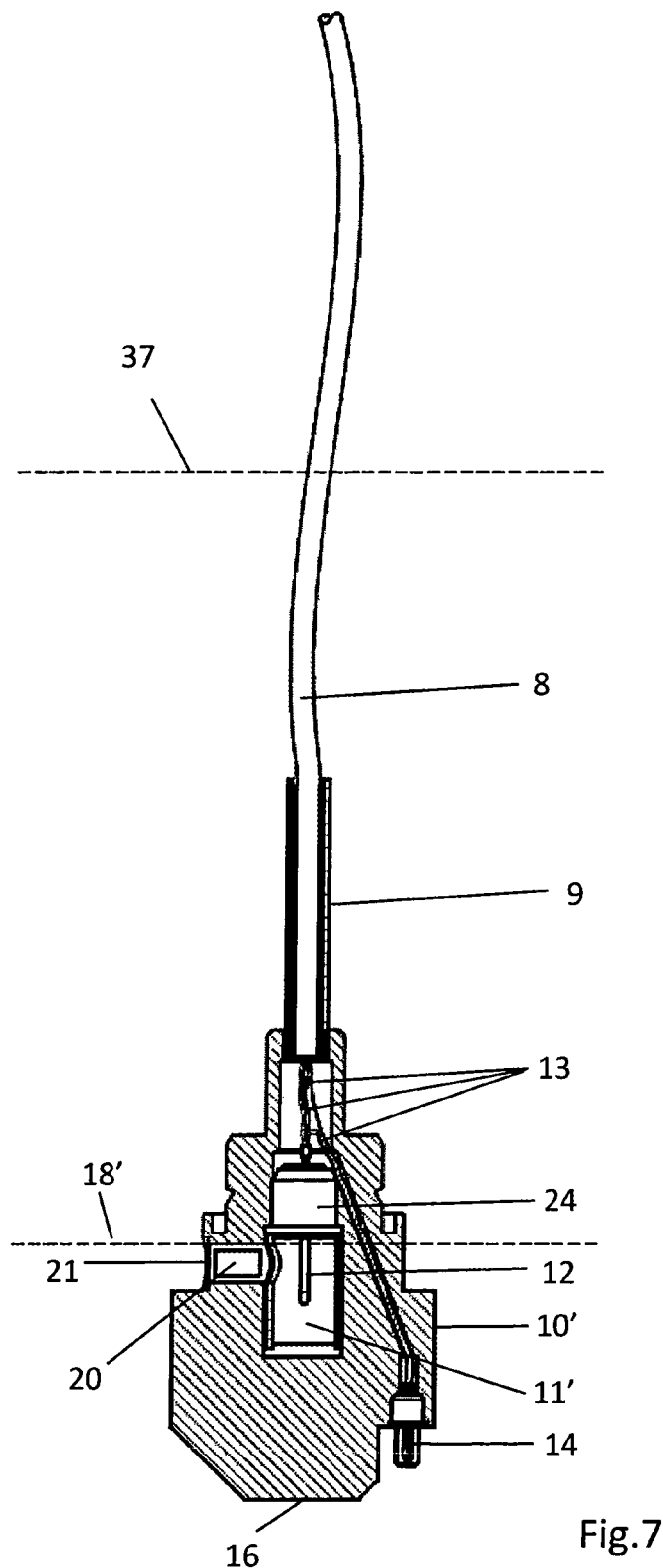
FIG. 7 is a side elevation sectional view of an additional drop-in probe according to an embodiment of the invention.

In FIG. 7 the measurement head 10' already described in FIG. 3 is shown again. In contrast to measurement head 10', it is now emphasized according to the invention that the total density of the measurement head arises from another plane 37. At the outlet point, a part of the cable 8 is also immersed in the molten steel and thus must be taken into account in the calculation of the total density of the measurement head. According to the invention, the measurement head should be immersed approximately 20 cm under the surface of the liquid steel and its measurement should be taken. As already described, molten steel here flows through the inlet opening 19, 20, 22 into the sample chamber 11'. Any gas can escape from the measurement head through an outlet opening through the refractory material 24 between the signal cable 8 and the metal tube 9. Here it is essential that the outlet opening be arranged higher than the inlet opening 19, 20, 22 of the sample chamber. In the scope of the invention, the term "higher" here means the different arrangement of the outlet or inlet opening along a longitudinal axis of the measurement head. Here, the inlet opening is arranged in the measurement head such that, for proper immersion of the measurement head in the molten steel, some flows first into the inlet opening and/or the sample chamber is filled through the inlet opening.

One advantageous embodiment of the invention distinguishes itself in that the total density—formed from the mass and the volume of the part of the entire drop-in probe immersed in the molten steel and in the slag is less than 7 g/cm$^3$. With this embodiment variant, the measurement head also comprises parts of the signal cable 8 and a metal tube 9 at least partially surrounding the signal cable 8, in so far as these components of the drop-in probe are immersed into the molten steel and in the slag.

According to experience, the slag on the liquid molten steel has a thickness of approximately 30 cm. It has thus proven especially advantageous if a cable length of 50 cm—composed of a thickness of the slag of approximately 30 cm and the sample location of approximately 20 cm at a density of the cable of approximately 1.6 g/cm$^3$—is included in the calculation of the total density of the measurement head. In one advantageous variant of this type of construction, a drop-in probe is obtained in which the total density of the measurement head and 50 cm of a signal cable 8 having a cable density of 1.6 g/cm$^3$ and also of a metal tube 9 at least partially surrounding the signal cable 8 equals less than 7 g/cm$^3$. In this way, it can be ensured that the measurement head is immersed in a reliable and reproducible way into the molten steel, in order to be used accordingly for the measurement of the properties of the melt. Thus, in this embodiment, the part of the drop-in probe immersed in the molten steel and/or in the slag has a total density of less than 7 g/cm$^3$. In this embodiment variant, the measurement head also comprises a metal tube 9 at least partially surrounding the signal cable. The location where the signal cable 8 leaves this metal tube 9 is the cable outlet. In the embodiment shown in FIG. 7, the cable outlet is also simultaneously the discharge opening—also called outlet opening.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A drop-in probe for determining phase changes by thermal analysis of a sample removed from a molten steel, the drop-in probe comprising a measurement head having an immersion end, a sample chamber arranged in the measurement head and having an inlet opening, a thermocouple projecting with its hot solder joint into the sample chamber, and a cable bushing for signal cables of the thermocouple, the cable bushing emerging from the measurement head out of a discharge opening on an end of the measurement head opposite the immersion end, the thermocouple being held in the sample chamber with a gas-permeable material,
wherein the cable bushing and the discharge opening are connected to the sample chamber in a gas permeable way via the gas-permeable material,
wherein a longitudinal axis of the measurement head extends between the immersion end and the discharge opening and a plane extends through the measurement head perpendicular to the longitudinal axis between the immersion end and the discharge opening, a portion of the measurement head which is bounded between the immersion end and the plane having a density of at least 7 g/cm$^3$,
wherein the inlet opening opens in a surface of the measurement head distal from the immersion end and proximate to the plane, and
wherein a total density of the measurement head equals less than 7 g/cm$^3$.

2. The drop-in probe according to claim 1, wherein the plane extends through a part of the inlet opening arranged farthest away from the immersion end.

3. The drop-in probe according to claim 1, wherein the inlet opening has a diameter that equals at least one third of a diameter of the sample chamber and is no larger than the diameter of the sample chamber.

4. The drop-in probe according to claim 1, wherein the thermocouple extends approximately parallel to the longitudinal axis with its hot solder joint in a direction of the immersion end.

5. The drop-in probe according to claim 1, wherein a tube, optionally a metal tube through which the signal cables are guided, is arranged on the discharge opening, the metal tube running coaxial to the longitudinal axis of the measurement head.

6. The drop-in probe according to claim 1, wherein the entrance of the inlet opening has a protective cap formed from metal or a combination of metal with cardboard or with paper.

7. The drop-in probe according to claim 6, wherein the protective cap comprises steel having a thickness of at most 0.5 mm or a combination of zinc with cardboard or with paper.

8. The drop-in probe according to claim 1, wherein the inlet opening is formed of quartz glass, the inlet opening optionally having a deoxidizing agent arranged therein.

9. The drop-in probe according to claim 1, further comprising an additional temperature sensor.

10. The drop-in probe according to claim 9, wherein the additional temperature sensor is arranged on the end of the measurement head opposite the immersion end.

11. A drop-in probe for determining phase changes by thermal analysis of a sample removed from a molten steel, the drop-in probe comprising a measurement head having an immersion end, a sample chamber arranged in the measurement head and having an inlet opening, a thermocouple projecting with its hot solder joint into the sample chamber, a cable bushing for signal cables of the thermocouple, and a metal tube at least partially surrounding the signal cable, the cable bushing emerging from the measurement head out of a discharge opening on an end of the measurement head opposite the immersion end, the discharge opening being formed by a gap between the signal cable and the metal tube,
wherein a longitudinal axis of the measurement head extends between the immersion end and the discharge opening and a plane extends through the measurement head perpendicular to the longitudinal axis between the immersion end and the discharge opening, a portion of the measurement head bounded between the immersion end and the plane having a density of at least 7 g/cm$^3$,
wherein the inlet opening opens at the plane, between the plane and the immersion end, or at the immersion end, and
wherein a total density of the measurement head, including the metal tube a part of the signal cable, equals less than 7 g/cm$^3$.

12. The drop-in probe according to claim 11, wherein the part of the signal cable included in the total density of the measurement head of less than 7 g/cm$^3$ is immersible in the molten steel and in a slag layer located on the molten steel during operation of the drop-in probe.

13. The drop-in probe according to claim 12, wherein the part of the signal cable included in the total density of the measurement head of less than 7 g/cm$^3$ is 50 cm long for an average cable density of 1.6 g/cm$^3$.

14. The drop-in probe according to claim 11, wherein the plane extends through a part of the inlet opening arranged farthest away from the immersion end.

15. The drop-in probe according to claim 11, wherein the inlet opening has a diameter that equals at least one third of a diameter of the sample chamber and is no larger than the diameter of the sample chamber.

16. The drop-in probe according to claim 11, wherein the thermocouple extends approximately parallel to the longitudinal axis with its hot solder joint in a direction of the immersion end.

17. The drop-in probe according to claim 11, wherein the thermocouple is held in the sample chamber with a gas-permeable material.

18. The drop-in probe according to claim 11, wherein the metal tube is arranged on the discharge opening and extends coaxial to the longitudinal axis of the measurement head.

19. The drop-in probe according to claim 11, wherein the entrance of the inlet opening has a protective cap formed from metal or a combination of metal with cardboard or with paper.

20. The drop-in probe according to claim 11, wherein the inlet opening is formed of quartz glass, the inlet opening optionally having a deoxidizing agent arranged therein.

21. The drop-in probe according to claim 11, further comprising an additional temperature sensor.

22. A drop-in probe for determining phase changes by thermal analysis of a sample removed from a molten steel bath, the drop-in probe comprising a measurement head having an immersion end, a sample chamber arranged in the measurement head and having an inlet opening, a thermocouple projecting into the sample chamber, a signal cable, and a cable bushing for the signal cable the cable bushing projecting from the measurement head out of a discharge opening on an end of the measurement head opposite the immersion end, wherein a longitudinal axis of the measurement head extends between the immersion end and the discharge opening, wherein a first plane extends through the measurement head perpendicular to the longitudinal axis at a position of the inlet opening which is farthest away from the immersion end, a portion of the measurement head which is bounded between the immersion end and the first plane having a density of at least 7 g/cm$^3$, and wherein a second plane extends through the measurement head perpendicular to the longitudinal axis at a position of the discharge opening or 0.5 meters away from the discharge opening, a body of the measurement head which is bounded between the immersion end and the second plane having a density of less than 7 g/cm$^3$.

* * * * *